United States Patent [19]

Jacobson et al.

[11] Patent Number: 5,558,097
[45] Date of Patent: Sep. 24, 1996

[54] METHOD FOR TACHYARRHYTHMIA DETECTION

[75] Inventors: Peter Jacobson, Haguenau; Daniel Kroiss, Schweighouse-Moder, both of France

[73] Assignee: ELA Medical S.A., Montrouge, France

[21] Appl. No.: 287,843

[22] Filed: Aug. 9, 1994

[30] Foreign Application Priority Data

Aug. 13, 1993 [FR] France ................................. 93 09950

[51] Int. Cl.$^6$ .................................................. A61B 5/0464
[52] U.S. Cl. ............................................................ 128/705
[58] Field of Search ..................................... 128/705, 702

[56] References Cited

U.S. PATENT DOCUMENTS

| | | |
|---|---|---|
| 4,184,493 | 1/1980 | Langer et al. |
| 4,393,877 | 7/1983 | Imran et al. ............................. 128/705 |
| 4,559,946 | 12/1985 | Mower. |
| 4,708,144 | 11/1987 | Hamilton et al. |
| 4,819,643 | 4/1989 | Menken. |
| 4,880,004 | 11/1989 | Baker et al. |
| 4,940,054 | 7/1990 | Grevis et al. |
| 4,967,747 | 11/1990 | Carroll et al. |
| 5,117,824 | 6/1994 | Keimel et al. |
| 5,188,117 | 2/1993 | Steinhaus et al. ...................... 128/708 |
| 5,339,820 | 8/1994 | Henry et al. ............................ 128/696 |

FOREIGN PATENT DOCUMENTS

| | | | |
|---|---|---|---|
| 0549438A1 | 12/1992 | European Pat. Off. | ......... A61N 1/08 |
| 89/03705 | 5/1989 | WIPO | ............................ A61N 1/365 |

OTHER PUBLICATIONS

Winkle, R., "State-of-the-Art of the Acid", May 1991, Part III, Pace, vol. 14, pp. 961–966.

Sperry et al., "Failure of a Second and Third Generation Implantable Cardioverter Defibrillator to Sense Ventricular Tachycardia: Implications for Fixed-Gain Sensing Devices", May 1992, Pace, vol. 15, 749–755.

*Primary Examiner*—William E. Kamm
*Assistant Examiner*—Scott M. Getzow
*Attorney, Agent, or Firm*—Orrick, Herrington & Sutcliffe

[57] ABSTRACT

A method and apparatus for optimizing the sensing circuit of a tachyarrhythmia detector for use with direct heart (cardiac) electrodes. The method is applied to detection of ventricular fibrillation and multifocal ventricular tachyarrhythmia, with rejection of T wave and pacing artifact. The sensing circuit optimized with this method includes a third-order high-pass filter followed by at least one comparator, with the filter corner frequency near 16 Hz and the comparator threshold near 0.40 mV referred to the input, in-band.

29 Claims, 2 Drawing Sheets

METHOD FOR TACHYARRHYTHMIA DETECTION

FIELD OF THE INVENTION

This invention relates to sensing circuits for tachyarrhythmia detectors, and more particularly to sensing circuits for implantable tachyarrhythmia detectors using direct heart (cardiac) electrodes.

BACKGROUND OF THE INVENTION

Implantable defibrillators, cardioverters, and antitachycardia pacemakers, or devices which combine two or more of these functions, require tachyarrhythmia detectors. The objective of the detector is to detect and signal the occurrence of a cardiac depolarization in the tissue adjacent to one or more electrodes in contact with or in proximity to the heart. Direct cardiac leads are those in such contact with heart tissue, as contrasted to electrodes that are non-invasive, i.e., secured to the skin, to monitor electrical cardiac activities.

It is essential to blank (isolate) the sensing amplifier of detection to protect against saturation due to pacing pulses, and to provide other types of protection against damage or malfunction due to external interference sources. These techniques are familiar to those skilled in the art, and are outside the scope of the below-described invention. Similarly, it is important to provide symmetric positive and negative comparator thresholds, or full wave rectification and a single comparator, for detecting both signal polarities. These techniques also are familiar to those skilled in the art, and are outside the scope of the below-described invention.

Langer U.S. Pat. No. 4,184,493 refers to a sensing circuit for an implantable defibrillator, having an amplifier, a first-order high-pass filter (the corner frequency is undisclosed), a bidirectional comparator, and a circuit which measures the fraction of time that the comparator asserts its output. The detector measures the average fraction of time when the ECG exhibits a high slope, compared to the fraction of time when the ECG exhibits a low slope. The circuit provides feedback to adjust amplifier gain automatically to maintain constant amplitude at filter output.

Imran U.S. Pat. No. 4,393,877 refers to a sensing circuit for an implantable defibrillator, which includes a slew rate detector circuit and a zero-crossing detector circuit. The slew rate detector has an amplifier, a first-order high-pass filter (corner frequency undisclosed), a unidirectional comparator, and a monostable multivibrator for timing a refractory period. The Imran circuit provides feedback to adjust amplifier gain automatically, to maintain constant amplitude at the filter input.

Mower U.S. Pat. No. 4,559,946 refers to a sensing circuit for an implantable defibrillator, which includes a slew rate sensitive circuit followed by a comparator. The Mower circuit provides feedback to adjust automatically, the comparator threshold to a fraction of recent peak filter output Menken U.S. Pat. No. 4,819,643 refers to a defibrillator with stimulation (pacing) and detection (sensing) functions, and a separate channel for the detection of fibrillation with automatic gain control, which delays the stimulation until the gain of the fibrillation detection channel reaches its maximum sensitivity. Menken does not provide any details of the bandwidth of the amplifier.

Grevis U.S. Pat. No. 4,940,054 refers to a defibrillator having an amplifier with at least two values of sensitivity, which are selected as a function of the type of rhythm detected. Grevis does not provide any details of the bandwidth of the amplifier.

Baker U.S. Pat. No. 4,880,004 refers to a circuit for arrhythmia detection, which includes an input amplifier having a bandwidth that is not specified, followed by a sensing channel with a high-pass filter at 25 Hz, and a measuring channel with additional high-pass filtering at 12 Hz. Each channel is followed by comparators. The Baker circuit provides feedback to adjust amplifier gain automatically to maintain constant the sensing margin (the amount by which the signal in the sensing channel exceeds its threshold). Due to the additional filtering in the measuring channel, this margin improves at low frequencies.

Carroll U.S. Pat. No. 4,967,747 refers to an implantable defibrillator with a sensing circuit a switched capacitor gain/filter block with an unspecified bandwidth, designed to provide glitch-free gain changes for automatic gain control.

Keimel U.S. Pat. No. 5,117,824 refers to an implantable circuit for stimulation and detection with automatic gain control, but which does not adjust the threshold after the stimulation. Keimel does not provide any details of the bandwidth of the amplifier.

In "State-of-the-Art of the AICD", *Pace*, May 1991, Winkle refers to a defibrillator without automatic gain control, for which "programming sensitivity requires great care at time of implantation and during follow-up to be certain that T waves are not oversensed and most importantly that ventricular fibrillation/tachycardia is not undersensed."

In "Failure of a Second and Third Generation Implantable Cardioverter to Sense Ventricular Tachycardia: Implications for Fixed-Gain Sensing Devices", *Pace*, May 1992, Sperry et al. wrote that "more sensitive fixed-gain settings or automatic-gain sensing are needed to detect low amplitude signals on a consistent basis. The undesirable aspect of using such high sensitivity is that of oversensing (e.g. T waves) by the device resulting in an increased risk of inappropriate discharges. Failure to sense ventricular fibrillation has however also been reported with automatic gain devices as well."

The inventors have recognized that a sensing circuit for a tachyarrhythmia detector needs to detect cardiac depolarizations, but reject undesired signals, including cardiac repolarization (T wave), and including signals emanating from the return to equilibrium of the electrode system and the pacemaker's output circuit after pacing, called pacing artifact. The aforementioned prior art techniques consist of high pass filters, refractory periods, and automatic gain or threshold control; but shortcomings exist for each of these, as follows.

Shortcomings of high pass filters: A filter for an implantable life-support device should have minimum complexity necessary to meet two performance criteria: Acceptably low probabilities of (i) rejecting desired signals and (ii) detecting undesired signals. None of the prior art patents discloses any systematic method for selecting filter characteristics (parameters) such as order, quality factor Q, and corner frequencies, to meet preselected performance criteria, with minimally complex hardware.

Shortcomings of refractory periods: If designers select a refractory period length sufficiently short to permit detection of tachyarrhythmias, then it turns out the refractory period does not cover T-waves at low heart rates (the time from depolarization to repolarization increases with decreasing heart rate). If refractory periods alone sufficed, the prior art devices would not provide additional complex automatic gain or threshold control.

Shortcomings of automatic gain or threshold control: Detectors can improve selectivity (the probability of rejecting undesired signals) and sensitivity (the probability of detecting desired signals) with this technique, only when a detected characteristics of recent events are good predictors of the same characteristics in future events.

There thus remains a need for improvement in the detection (sensing) response of implantable defibrillators.

STATEMENT AND SUMMARY OF THE INVENTION

The inventors have realized that, although designers of bradycardia pacemakers (which speed up the heart to normal rhythms) know that the amplitude of a normally conducted heartbeat (R wave) predicts the amplitude of the next R wave with good correlation, designers of tachycardia detectors need to ask two additional questions:

1. How well does the amplitude of the desired signal (tachyarrhythmia depolarization) predict the amplitude of the next desired signal?
2. How well does the amplitude of the desired signal (again, tachyarrhythmia depolarization) predict the amplitude of the next undesired signal (repolarization or pacing artifact)?

To respond to the first question, consider the nature of ventricular fibrillation, as detected by bipolar electrodes directly on the surface of the heart. The detector cannot afford to miss sensing ventricular fibrillation, the deadliest of tachyarrhythmias. Implantable tachyarrhythmia detectors normally use bipolar endocardial or epicardial electrodes because of their good far-field rejection compared to unipolar electrodes.

Ventricular fibrillation consists of "wandering wavelets", multiple small depolarization fronts moving randomly around the cardiac surface in all directions. The amplitude detected when a wavelet passes bipolar electrodes depends on the vector component of the wavelet which lies along the axis of the bipolar electrodes (a wavelet traveling perpendicular to the axis of the electrodes produces zero amplitude since it strikes both electrodes simultaneously; conversely a wavelet traveling along the axis produces maximum amplitude since it strikes first one electrode and then the other). Measurements made with human ventricular fibrillation or multifocal ventricular tachycardia detected with bipolar electrodes show near zero correlation between the amplitude of one detected complex and the next.

To respond to the second question, the inventors measured R wave and T wave amplitude in twenty patients with endocardial bipolar electrodes. Correlation of T wave amplitude with R wave amplitude measured only 50%.

Why in the face of these facts do many prior art designs rely on automatic gain control? First because some small correlations do exist, so this technique may somewhat improve performance statistically. Perhaps also because many publications have observed that ventricular fibrillation detected on the surface of the body (not the surface of the heart) decreases in amplitude as fibrillation proceeds. This occurs because the "wandering wavelets" become smaller and more disorganized, so the electrical sum of all of them, seen at the surface, decreases with time. However, a designer should not expect the same thing to happen with direct heart electrodes.

The inventors also have realized that automatic gain or threshold control, and refractory periods, cannot provide a complete solution to the problem of tachyarrhythmia detection with direct heart electrodes, and that the designer must also systematically optimize filtering for sensitivity and selectivity; but no prior art teaches or suggests how to do this.

Since the detection circuit will form part of an implantable device, the designer should minimize power consumption to prolong battery life, and minimize complexity (and part count) to reduce implant size. Generally in microcircuit power design, increasing either the gain or the bandwidth of an amplifier and filter combination requires a proportionate increase in power consumption. Thus the detection circuit should operate with minimum (gain)*(bandwidth) product, and minimum component size and count.

It is therefore, an object of the present invention to provide for optimizing the design of a tachyarrhythmia detecting circuit for use with direct heart electrodes, particularly in implantable devices. It is a further object of this invention to provide a quantitative method for examining the effect of design parameters on one or more of the following criteria: sensitivity, selectivity, (gain)*(bandwidth) product, and component count.

Another object of the invention is to apply the optimization method to the design of a circuit for detecting ventricular tachyarrhythmias and rejecting T waves and pacing artifacts.

Broadly, the present invention is directed to the selection of filter characteristics and a comparator threshold for a tachyarrythmia detector circuit having a filter and comparator, to distinguish desired and undesired signals. The invention can be equally well applied to systems with additional blanking (absolute refractory period), interference protection, rectification, and/or symmetric comparator thresholds. The field of application of this invention includes sensing circuits for atrial or ventricular arrhythmia detection.

In its application to the aforementioned problems, one aspect of the invention concerns a detection circuit which includes:

a third order high-pass filter, with a corner frequency of approximately 16 Hz; and a comparator connected to filter output, with a threshold of approximately 0.40 mV, in-band referenced to the filter input. The term "in-band" refers to signals within the passband of the filter.

Another aspect of the present invention is directed to a process for optimizing a detection circuit for the detection of tachyarrhythmia, in which the circuit includes at least a filter followed by a comparator. One such method includes the steps of:

obtaining samples of desired signals and undesired signals;

determining the peak amplitude of the filter output for the desired signal samples and undesired signal samples as a function of a filter characteristic value;

determining the relationship of the combinations of the filter characteristic value and the threshold that provide the desired sensitivity and selectivity; and selecting the combination of the filter characteristic value and the comparator threshold value that translate into the minimal value of the gain times the bandwidth.

In a preferred embodiment, the method further includes the steps of repeating the process with filters of different order and selecting the filter of the lowest order that satisfies the predetermined requirements for sensitivity and selectivity.

According to the invention, samples of desired signals include multifocal ventricular tachycardia and ventricular fibrillation, and samples of the undesired signals include T waves and pacing artifacts. Preferably, the filter characteristic value is the corner frequency of a high-pass filter.

Another aspect of the present invention is directed to a circuit for detecting tachyarrhythmia which includes a high-pass filter of the third order and a comparator having a threshold which is connected to the filter output. Preferably, the filter presents a corner frequency of approximately 16 Hz, and the comparator threshold is programmable or is automatically adjusted to 0.40 mV.

BRIED DESCRIPTION OF THE DRAWINGS

Further features of the invention, its nature and various advantages, will be apparent from the accompanying drawings and the following detailed description of the invention, in which like reference characters refer to like elements, and in which.

DETAILED DESCRIPTION OF THE INVENTION

Figure 1:
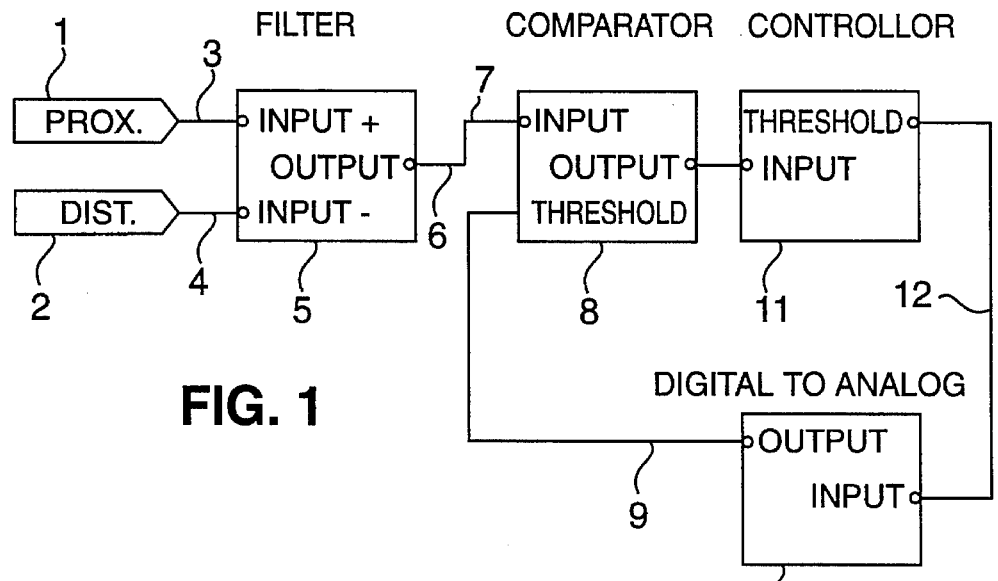
FIG. 1 shows a schematic block diagram of a sensing circuit in accordance with a preferred embodiment of the present invention.

FIG. 1 shows a sensing circuit for a tachyarrhythmia detector according to the present invention. Bipolar direct heart electrode terminals 1 and 2 bring the cardiac signal over leads to the differential inputs 3, 4 of filter 5. Filter 5 is optimized for sensitivity and selectivity following the method of the invention, as described below. Filter 5 has an output 6 connected to one input 7 of comparator 8. The other input 9 of comparator 8 is connected to a reference voltage, provided in the preferred embodiment by a digital to analog converter 10.

A controller 11 has a digital output 12 to set the comparator sensing threshold value provided at input 9 via digital to analog converter 10. Controller 11 also receives the output 13 of comparator 8, indicating when asserted that the sensing circuit detects a cardiac depolarization. Controller 11 can provide refractory periods, and via digital to analog converter 10 it can also provide automatic threshold control and/or programmable threshold control, as are well known to persons of ordinary skill in the art.

Figure 2:
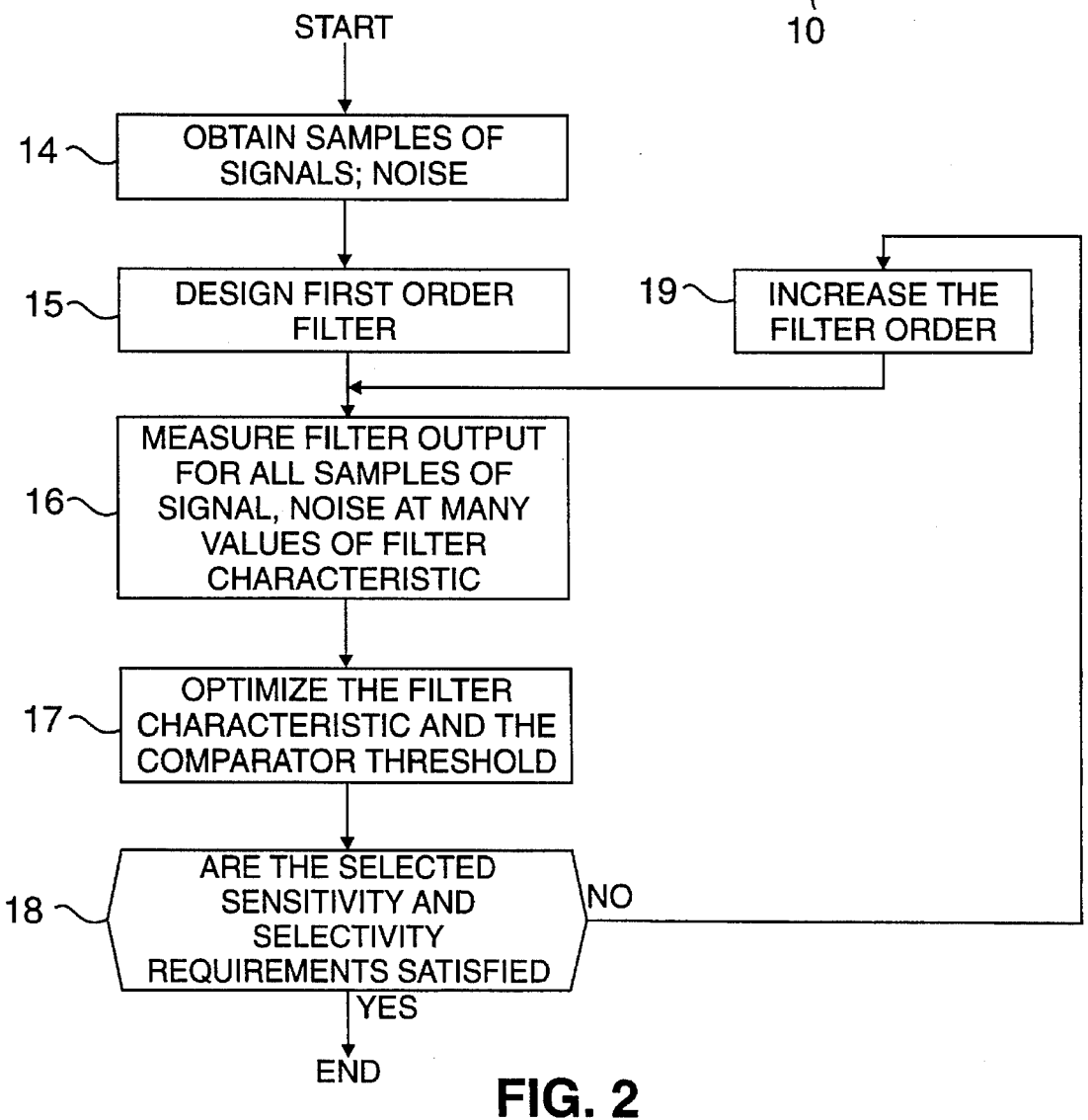
FIG. 2 shows a diagram of a method in accordance with a preferred embodiment of the present invention.

Referring to FIG. 2, a method for optimizing parameters of the sensing circuit shown in FIG. 1 is illustrated. The designer first obtains samples of the desired signals to be detected, and the undesired signals to be rejected, at step 14. In one embodiment, the desired signals include cardiac depolarizations from ventricular fibrillation and ventricular tachycardia, and the undesired signals include cardiac repolarizations (T waves) and pacing artifacts.

At step 15, the designer attempts to meet requirements with a simple first-order filter. At step 16, the designer measures filter output for each of the desired and undesired samples, and then repeats these measurements at different values of some preselected filter characteristic, such as the filter cutoff (or corner) frequency. At step 17, the designer takes these data and uses them to optimize this filter characteristic and the threshold of comparator 8.

Figure 3:
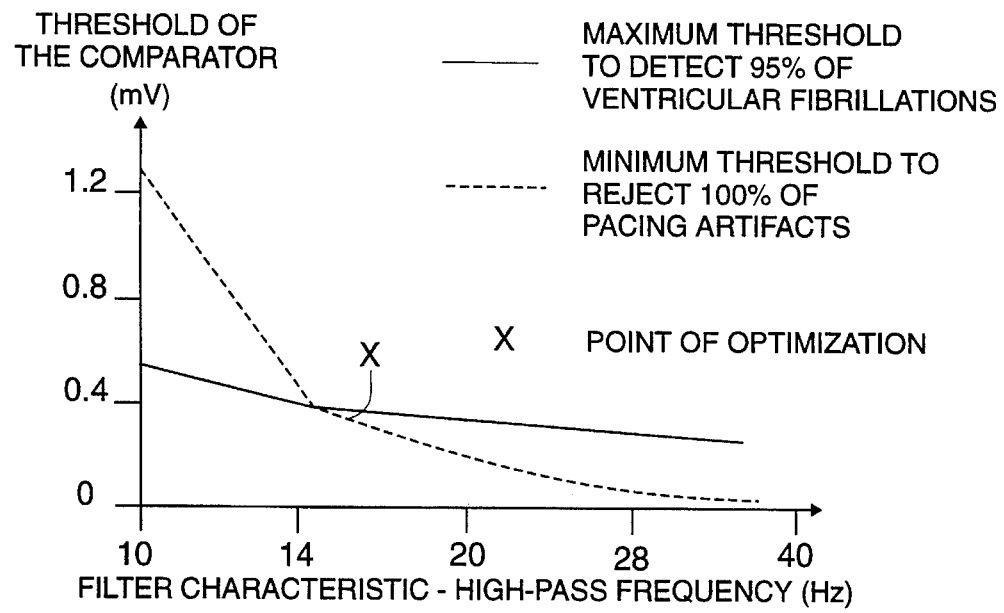
FIG. 3 shows an optimization curve for filter corner frequency and comparator threshold, with a third-order filter, in accordance with a preferred embodiment of the invention.

One optimization technique, shown in FIG. 3, is to measure and graph the lowest comparator threshold value which successfully rejects the required percentage of the undesired signals, and the highest comparator threshold which successfully detects the required percentage of the desired signals, both as a function of the preselected filter characteristic which was varied in step 16 (FIG. 2). FIG. 3 illustrates the optimization technique with examples of predetermined sensitivity and selectivity criteria, rejecting 100% of unwanted signals (a selectivity criterion) and detecting 95% of desired signals (a sensitivity criterion). Any points in the graph which are above the lowest threshold for rejection, and also below the highest threshold for detection, represent combinations of the comparator threshold and filter characteristic values which meet the predetermined sensitivity and selectivity requirements. After generating the curve of FIG. 3, the designer selects one optimal filter characteristic value and the corresponding comparator threshold value, out of the set of acceptable points.

In a preferred variant of the method of the invention, the designer selects the point with the lowest gain*bandwidth requirement. In the example of FIG. 3, this is the point with the highest comparator threshold which meets sensitivity and selectivity requirements (that is, below the solid line and above the dashed line).

Returning to FIG. 2, it may occur at step 17 that the designer cannot find any combination of filter characteristic and comparator threshold to meet sensitivity and selectivity requirements (e.g., the dashed line is everywhere above the solid line). If so, at step 18, the designer decides to increase filter order at 19 and then return to step 16 to attempt optimization with this more complicated filter. Increasing filter order increases component count. Thus, following the method of the invention, and perhaps using several different filter orders, the designer obtains an optimized sensing circuit of minimum complexity and gain*bandwidth product.

The inventors applied the method of the invention to the problem of detecting ventricular tachycardia and fibrillation while rejecting the T wave, with the predetermined requirements of rejecting 100% of T waves and sensing 95% of all true depolarizations. The inventors used the filter high-pass cutoff frequency as the preselected filter characteristic, which is varied in step 16. FIG. 3 shows that a third order filter is adequate for the predetermined sensitivity and selectivity, and is optimized for gain*bandwidth with high-pass corner frequency of approximately 16 Hz and in-band comparator threshold referenced to the filter 16 input, of approximately 0.40 mV.

Figure 4:
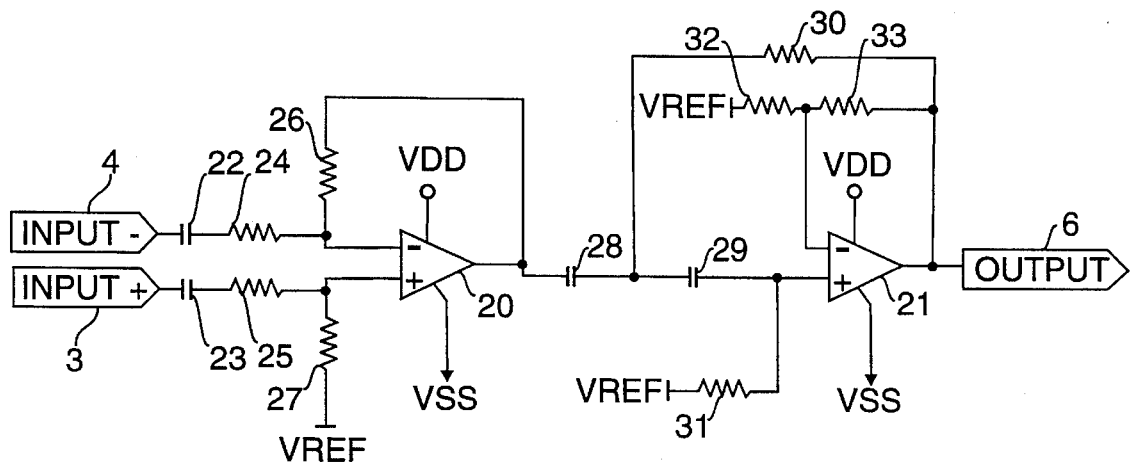
FIG. 4 show a schematic diagram of the filter of FIG. 1.

FIG. 4 shows an implementation of the filter derived using the method of the invention. Power supply circuits (not shown) provide voltage supplies VDD=0.0 V, VSS=−3.0 V, and VREF=−0.80 V. The filter has a first order stage using amplifier 20 and a second order stage using amplifier 21. The gain of the first stage is approximately 160, with a single high-pass corner at 16 Hz. The gain of the second stage is approximately 1.6, with a second order high-pass Butterworth response, also with a corner at 16 Hz. The table below gives typical values for resistors and capacitors in the filter.

TABLE

| Component | Type | Value | Notes |
| --- | --- | --- | --- |
| 22, 23 | capacitor | 0.10 uF | non polar |
| 24, 25 | resistor | 0.10 MOhm | |
| 26, 27 | resistor | 16 MOhm | |
| 28, 29 | capacitor | 1.0 nf | non polar |
| 30, 31 | resistor | 10 MOhm | |
| 32 | resistor | 15 MOhm | |
| 33 1 | resistor | 8.2 MOhm | |

Capacitor pair 22 and 23, and resistor pairs 24 and 25, and 26 and 27 should be closely matched for good common mode rejection.

FIG. 4 illustrates a classical filter with discrete resistors and capacitors, although a filter with the same characteristics could be integrated using switched-capacitor techniques commonly known to designers skilled in the art.

Such features as input protection against high energy sources such as defibrillators, or against high frequency sources such as electrosurgery, are not shown, since these have no bearing on the invention and are also commonly known.

Although the invention has been described with reference to a particular embodiment, it is to be understood that this embodiment is merely illustrative of the application of the principles of the invention. Numerous other modifications may be made and other arrangements may be devised without departing from the spirit and scope of the present invention.

We claim:

1. A method for optimizing a sensing circuit for a tachyarrhythmia detector, having at least one filter having an input for signals, a filter characteristic and an output, and at least one comparator having an input connected to the filter output and a threshold value input, comprising the steps of:

a) obtaining samples of desired and undesired signals;

b) determining a peak filter output amplitude for said samples of desired and undesired signals as a function of variations in a filter characteristic value;

c) determining a set of combinations of said filter characteristic values, and the threshold value of said comparator, which provide a preselected selectivity and sensitivity; and d) selecting a single combination of said filter characteristic value and comparator threshold value resulting in a minimum gain*bandwidth product.

2. The method of claim 1 wherein obtaining samples of said desired signals further comprises obtaining samples of multifocal ventricular tachycardia and ventricular fibrillation.

3. The method of claim 1 wherein obtaining samples of said undesired signals further comprises obtaining samples of T waves and pacing artifacts.

4. The method of claim 1 wherein said filter characteristic parameter is a high-pass corner frequency.

5. The method of claim 1 wherein obtaining samples of said desired signals further comprises obtaining samples of multifocal ventricular tachycardia and ventricular fibrillation, and wherein obtaining samples of said undesired signals further comprises obtaining samples of T waves and pacing artifacts.

6. The method of claim 5 further comprising the steps of:

e) repeating steps a)–d) wherein said one filter is replaced with at least one other filter, each other filter having a different order; and f) selecting the filter having the lowest order which satisfies the preselected sensitivity and selectivity.

7. The method of claim 5 wherein said filter characteristic parameter is a high-pass corner frequency.

8. The method of claim 7 further comprising the steps of:

e) repeating steps a)–d) wherein said one filter is replaced with at least one other filter, each other filter having a different order; and f) selecting the filter having the lowest order which satisfies the preselected sensitivity and selectivity.

9. The method of claim 1 wherein obtaining samples of said undesired signals further comprises obtaining samples of T waves and pacing artifacts, and wherein said filter characteristic parameter is a high-pass corner frequency.

10. The method of claim 9 further comprising the steps of:

e) repeating steps a)–d) wherein said one filter is replaced with at least one other filter, each other filter having a different order; and f) selecting the filter having the lowest order which satisfies the preselected sensitivity and selectivity.

11. The method of claim 1 wherein obtaining samples of said desired signals further comprises obtaining samples of multifocal ventricular tachycardia and ventricular fibrillation, and wherein said filter characteristic parameter is a high-pass corner frequency.

12. The method of claim 11 further comprising the steps of:

e) repeating steps a)–d) wherein said one filter is replaced with at least one other filter, each other filter having a different order; and f) selecting the filter having the lowest order which satisfies the preselected sensitivity and selectivity.

13. The method of claim 1 further comprising the steps of:

e) repeating steps a)–d) wherein said one filter is replaced with at least one other filter, each other filter having a different order; and f) selecting the filter having the lowest order which satisfies the preselected sensitivity and selectivity.

14. The method of claim 13 wherein obtaining samples of said undesired signals further comprises obtaining samples of T waves and pacing artifacts.

15. The method of claim 13 wherein said filter characteristic parameter is a high-pass corner frequency.

16. The method of claim 1 wherein obtaining sample of said desired signals further comprises obtaining samples of multifocal ventricular tachycardia and ventricular fibrillation, the method further comprising the steps of:

e) repeating steps a)–d) wherein said one filter is replaced with at least one other filter, each other filter having a different order; and f) selecting the filter having the lowest order which satisfies the preselected sensitivity and selectivity.

17. The method of claim 1 wherein step c) further comprises determining a lowest comparator threshold value which successfully rejects the predetermined selectivity for said filter characteristic values, and determining a highest comparator threshold value which successfully detects the predetermined sensitivity for said filter characteristic values.

18. A method for optimizing a sensing circuit for a tachyarrhythmia detector, having at least one filter having an input for signals, a filter characteristic and an output, and at least one comparator having an input connected to the filter output and a threshold value input, comprising the steps of:

a) obtaining samples of desired and undesired signals;

b) determining a peak filter output amplitude for said samples of desired and undesired signals as a function of variations in a filter characteristic value;

c) determining a set of combinations of said filter characteristic values, and the threshold value of said comparator, which provide a preselected selectivity and sensitivity;

d) selecting a single combination of said filter characteristic value and comparator threshold value resulting in a minimum gain*bandwidth product;

e) repeating steps a)–d) wherein said one filter is replaced with at least one other filter, each other filter having a different order; and f) selecting the filter having the lowest order which satisfies the preselected sensitivity and selectivity.

19. The method of claim 18 wherein obtaining samples of said desired signals further comprises obtaining samples of multifocal ventricular tachycardia and ventricular fibrillation.

20. The method of claim 19 wherein obtaining samples of said undesired signals further comprises obtaining samples of T waves and pacing artifacts.

21. The method of claim 20 wherein said filter characteristic parameter is a high-pass corner frequency.

22. The method of claim 19 wherein said filter characteristic parameter is a high-pass corner frequency.

23. The method of claim 22 wherein obtaining samples of said undesired signals further comprises obtaining samples of T waves and pacing artifacts.

24. The method of claim 18 wherein said filter characteristic parameter is a high-pass corner frequency.

25. The method of claim 24 wherein obtaining samples of said undesired signals further comprises obtaining samples of T waves and pacing artifacts.

26. The method of claim 25 wherein obtaining samples of said desired signals further comprises obtaining samples of multifocal ventricular tachycardia and ventricular fibrillation.

27. The method of claim 18 wherein obtaining samples of said undesired signals further comprises obtaining samples of T waves and pacing artifacts.

28. The method of claim 27 wherein obtaining samples of said desired signals further comprises obtaining samples of multifocal ventricular tachycardia and ventricular fibrillation.

29. The method of claim 27 wherein said filter characteristic parameter is a high-pass corner frequency.

* * * * *